United States Patent [19]

Krsek

[11] 4,254,008
[45] Mar. 3, 1981

[54] CROSSLINKED ACRYLAMIDE POLYMER COMPOSITIONS AND SHAPED ARTICLES THEREFROM

[75] Inventor: George Krsek, Culver, Ind.

[73] Assignee: Diamond Shamrock Corporation, Dallas, Tex.

[21] Appl. No.: 75,021

[22] Filed: Sep. 13, 1979

Related U.S. Application Data

[63] Continuation of Ser. No. 974,007, Dec. 28, 1978, abandoned.

[51] Int. Cl.$^3$ .............................................. C08K 5/05
[52] U.S. Cl. ................................ 260/33.4 R; 128/283
[58] Field of Search .................. 260/29.4 UA, 29.6 E, 260/33.2 R, 33.4 R; 128/283

[56] References Cited

U.S. PATENT DOCUMENTS

| | | | |
|---|---|---|---|
| 3,062,776 | 11/1962 | Gaylord | 260/33.4 R |
| 3,081,277 | 3/1963 | Wohnsiedler | 260/33.2 R |
| 3,242,111 | 3/1968 | Michelotti | 260/33.4 R |
| 4,078,568 | 3/1978 | Etes | 128/283 |
| 4,080,358 | 3/1978 | Krumel | 260/33.2 R |
| 4,153,055 | 5/1979 | Etes | 128/283 |

*Primary Examiner*—Paul R. Michl
*Attorney, Agent, or Firm*—Stuart L. Melton

[57] ABSTRACT

An improved ostomy seal is provided by a crosslinked composition comprising a water-soluble acrylamide polymer, a plasticizing quantity of a water-miscible polyol (containing water) that provides an elastomeric gel, and a crosslinking polyaldehyde.

10 Claims, No Drawings

CROSSLINKED ACRYLAMIDE POLYMER COMPOSITIONS AND SHAPED ARTICLES THEREFROM

RELATED APPLICATIONS

This application is a continuing application of copending application Ser. No. 974,007, filed Dec. 28, 1978 now abandoned.

BACKGROUND OF THE INVENTION

This invention relates to crosslinked acrylamide polymer compositions and shaped polymeric products derived therefrom suitable for application to human skin. More particularly, it is directed to ostomy sealing means (hereinafter called "ostomy seals") made from particular crosslinked compositions having a good balance of physical properties and improved resistance to degradation in service.

The term "Ostomy" has come into use to define, in a broad sense, the surgical procedures known as colostomy, ileostomy, cecostomy, ureterostomy, ileal conduit, ileal bladder, wet colostomy, etc. This surgery usually results in an artificial opening through the abdominal wall for the terminal end of the intestine or a duct, called a stoma, to discharge the body wastes of feces or urine.

Many ostomy devices or appliances have been developed through the years to aid the ostomy patient. Typical of such devices are ostomy bags or pouches constructed of flexible plastic or rubber materials, for receiving and holding these body wastes. In use it is necessary that a liquid-proof seal be maintained between the patient's skin and the bag (or retainer plate to which the bag may be attached) to prevent leakage of the waste material onto the skin of the patient surrounding the stoma or even therebeyond. In addition to the odor that would result from such leakage, irritation of the peristomal skin of the patient surrounding the stoma is extremely likely under circumstances of leakage, and in ileostomy cases, where the discharge is from the small intestine, digestive liquids can actually digest the skin of the patient if they come in contact with it.

Consequently, extensive efforts have been directed to developing sealing materials and means that provide effective liquid-tight seals with minimum irritation to the peristomal skin. Ideally an ostomy seal should be soft and flexible so as to conform to the body, yet have sufficient elasticity and recovery to firmly engage the stoma. It should be non-allergenic, non-irritating and non-sensitizing; and desirably possess visual appeal and freedom from odor. Further, it should be resistant to acids, bases, enzymes and other materials which may be found in intestinal and urinary discharges. Lastly, and possibly most critical, it should be capable of absorbing moisture from the skin and from any body wastes it contacts, without disintegrating or developing a slimy surface so as to maintain useful and serviceable cohesive and adhesive properties. Of equal importance, all these properties must be provided with sealing compositions that are both economical and easily fabricated into ostomy seals, which may be in the form of pads, gaskets, rings and the like as is well-known to the art.

SUMMARY OF THE INVENTION

While a number of compositions have been developed for ostomy seals, none satisfy all the prerequisites of an ideal seal. Consequently, it is an object of this invention to provide an improved ostomy seal (and ostomy appliances utilizing such a seal) that more completely and nearly satisfies these requirements. These and still other objects and advantages, which will become apparent from the following description and claims, are attained with an ostomy seal that is made with a composition comprising: a water-dispersible acrylamide polymer; a quantity, rendering the composition soft and elastomeric, of a solvating water-miscible polyol, or mixture of polyols, containing water; and a crosslinking polyaldehyde. After the composition is formed into the desired seal configuration, the seal is treated to effect crosslinking of the acrylamide polymer and thereby renders it substantially insoluble in water.

DETAILED DESCRIPTION

In the following description and claims, all parts and percentages are by weight.

The acrylamide polymer used in the invention ostomy seal composition is a water-dispersible acrylamide or methacrylamide polymer or copolymer capable of forming at 1% total solids a true aqueous solution and/or a stable hydrocolloidal dispersion. It has been found that "nonionic" virtual homopolymers of acrylamide (containing no more than about four percent by weight sodium acrylate) having high molecular weight, such as Reten 420 (Hercules), give seals having, after being crosslinked, 350% or less water swelling (as measured by weight gain) after 24 hours water immersion and, hence, constitutes a preferred embodiment. On the other hand, copolymers containing appreciable quantities of anionic groups (such as Reten 421 and 425 containing 10 percent or more of sodium acrylate) or cationic groups (such as Reten 210 and 220 containing 10 percent or more of betamethacryloyloxyethyltrimethyl ammonium methyl sulfate) give seals, after crosslinking, swelling about 2,250% (Reten 421), 3,800% (Reten 425) and 1,050% (Reten 210). Consequently, for minimum water swellability, the total weight of monomer units having anionic and/or cationic functionality in the copolymer of mixture of copolymers utilized in the invention seals preferably will not exceed about 5 percent of the total weight of acrylamide and/or methacrylamide polymers employed; and, ideally, will not exceed about 2 percent of the total weight of the polymer or mixture of polymers for lowest water sensitivity. Equally satisfactory, are copolymers of a major portion of acrylamide and/or methacrylamide (51-100 percent) and a minor portion (0-49 percent) of a copolymerizable vinyl monomer or monomer mixture, free of ionic groups, in a quantity not significantly diminishing the polymer's water dispersibility. Useful vinyl comonomers may be styrene, vinyl acetate, acrylonitrile, methyl vinyl ether, vinyl pyrolidone, beta-hydroxyl ethyl and propyl acrylates, methyl acrylate, methyl methacrylate, beta-hydroxy ethyl and propyl methacrylates, vinylidene chloride, and the like, and even divinyl monomers such as divinyl benzene, methylenebisacrylamide, and N,N-diallyl-acrylamide, if employed in a quantity small enough (e.g., up to about 5 weight percent) not to disrupt the water dispersibility of the acrylamide polymer. Finally, while acrylamide and/or methacrylamide polymers and copolymers are preferred, water-dispersible polymers and copolymers of N-substituted acrylamide or methacrylamide such as N-methyl acrylamide, N-methyl methacrylamide, N-methylol acrylamide, N-methylol methacrylamide and N-isopropyl acrylamide may also be used. Hence, in the following description and in the claims, it should be understood that the expression "acrylamide polymer" is used in the generic sense to encompass not only the virtual homopolymers of acrylamide or methacrylamide, but also water-dispersible polymers and copolymers of N-substituted acrylamide or methacrylamide, which are capable of being crosslinked with polyaldehydes, as well as mixtures of any of these polymers. The molecular weight of the acrylamide polymer should be high enough so as to give an ostomy seal having, after crosslinking, substantially elastomeric-like properties. Typically, useful polymers have given one percent aqueous solutions (or gels) at 25° C. having a Brookfield viscosity of about 10 centipoises or more, and a range of particle sizes such that virtually none is retained on a No. 20 U.S. mesh screen, while about 90–100 percent is retained on a No. 100 U.S. mesh screen. Polymers having smaller particle sizes may be used, but will gel faster and, hence, may require a compensating reduction in the water level of the polyol(s) and/or temperature of gellation. Because of this, they may be preferred when only a small amount of water, e.g., 1 to 2 percent, is used in the solvating polyol(s).

The water-miscible polyol, or mixture of polyols, containing water that is used to solvate and plasticize the acrylamide polymer is chosen to provide a seal composition that is soft, flexible and elastomeric and has no tactile surface exudation of polyol after gellation and crosslinking. Because of its excellent solvating properties and low toxicity and absorption into the skin, glycerine is the preferred polyol. It may be used either by itself or combined with other water-miscible polyols— either of the primary (solvating) or secondary (diluting) type. Other suitable solvating polyols include ethylene glycol, diethylene glycol, and sorbitol (when it is used with sufficient water and/or other polyols to provide a liquid mixture). Useful secondary water-miscible polyols include, without limitation, propylene glycol, dipropylene glycol, the butylene glycols, and polyethylene glycols (above diethylene glycol) having a molecular weight of up to about 600. Typically, the plasticizer mixture will comprise about 20–99 percent primary polyol, about 0–79 percent secondary polyol and about 1–20 percent water. The preferred level of water will vary depending on the type of primary polyol and percentage of secondary polyol used. For example, ethylene glycol and/or glycerine, alone, give excellent results with as little as 1 percent water, although 3–7 percent is typically used to accelerate gellation. Diethylene glycol, on the other hand, requires more water, typically 5–15 percent, for good solvating properties. Higher quantities of secondary polyol, as for example 20 percent or more, also necessitate the use of higher water levels, such as 5–15 percent if suitably rapid gellation is to be attained. Additionally, temperature affects the minimum level of water required: more being required when lower gelling temperatures are used. Finally, acrylamide polymers of higher molecular weight and/or less hydrophilic nature may require more water in the polyol plasticizer. In work to date, the best balance of seal properties coupled with good processing and gelling characteristics have been obtained with polyol plasticizer mixtures comprising about 50–99 percent glycerine, 0–49 percent secondary polyol, and 1–18 percent water. In the above discussion, the percent water includes, of course, not only water added to the polyol, but also that present in the polyol as purchased.

The quantity of polyol, or mixtures of polyols, containing water used is sufficient to provide a seal that is, as previously stated, soft and flexible and yet elastomeric. Illustrative of seal physical properties obtained are: Shore A, 1–5 (or Sponge Rubber Gauge values, 80–95); tensile strength at break, 16–22 psi; tensile modules, 12–30 psi; elongation at break 350–600 percent; crescent tear, 507 psi; and, compression modulus, 15–35 psi. Typically, about 125 to 200 parts of polyol(s) containing water per 100 parts of acrylamide polymer provides such properties, with about 150–175 parts being the generally preferred range. If the seal composition contains appreciable quantities of particulate fillers such as clay, calcium carbonate, calcium silicate, silicon dioxide and the like, or other types of water-dispersible polymers, as hereinafter described, quantities of polyol(s) in excess of 200 parts may be used or even be required to provide the desired softness and flexibility.

The invention ostomy seal is crosslinked with a polyaldehyde that is soluble, in the quantity employed, in the poly(s)-water mixture used to plasticize the acrylamide polymer. Suitable polyaldehydes include, without limitation, glyoxal, succinaldehyde, glutaraldehyde, 3-methyl glutaraldehyde, alpha-hydroxyadipaldehyde and the like. Alternatively, aldehyde bisulfite addition products, either preformed (e.g. glutaraldehyde bissodium bisulfite) or formed in situ in the polyol-water mixture at the time of formulating and admixing the seal composition, may be used. Such complexes are particularly preferred for providing about one-half or more of the polyaldehyde when diminished yellowing of the seal is desired. While as little as 0.1 part of polyaldehyde per 100 parts of the acrylamide polymer will usually provide acceptable crosslinking, 0.2–0.5 parts are typically employed to ensure adequate crosslinking, and hence acceptable decreased water sensitivity. While more than 0.5 parts may be used, the small additional crosslinking obtained generally does not justify the added cost. The type and quantity of polyaldehyde employed should, as pointed out above, be soluble in the polyol-water plasticizer mixture for maximum crosslinking efficiency. Further, mixtures of suitable polyaldehydes and/or aldehyde bisulfite addition products may be used.

When, as described above, it is desired to form the aldehyde bisulfite addition product in situ, sodium metabisulfite, or sodium bisulfite, and the polyaldehyde are admixed and dissolved in the polyol(s)-water plasticizer mixture prior to admixing the acrylamide polymer. To facilitate solvating and mixing, the bisulfite may first be predissolved in some or all of the water. Sodium bisulfite or the aldehyde bisulfite addition product provides two advantages. First, it lowers the vapor pressure and hence odor of the polyaldehyde during the mixing, fabrication and curing of the seal composition. Secondly, it acts as a color stabilizer to provide a seal composition having less tendency to yellow during the crosslinking treatment and/or in long-term storage, thus giving a seal having less discoloration. For maximum benefit, about 1.2 to 2 moles of the metabisulfite salt (or 2.4 to 4 moles of the bisulfite salt) are employed for every two aldehyde equivalents present in the polyaldehyde. Thus to obtain maximum whiteness with a dialdehyde crosslinker, 1.2 to 2 moles of sodium metabisulfite, or 2.4 to 4 moles of sodium bisulfite, would be used per mole of the dialdehyde. Lesser quantities of the bisulfite may be used, such as 0.5 to 1.2 moles of bisulfite per mole of aldehyde group, when some yellowing is acceptable. As is apparent, some or all the bisulfite (depending upon the ratio desired) may be supplied by a preformed aldehyde-bisulfite addition product of the polyaldehyde. When only color stabilization is desired, other antioxidants soluble, in the quantity employed, in the polyol-water mixture, such as ascorbic acid, hydroquinone, sodium thiosulfate and the like, may be used to replace, or sometimes supplement, the bisulfite salt as the color stabilizer.

In some instances, the seal composition is enhanced by including formaldehyde, either aqueous (e.g. 37 percent) or solid (e.g. paraformaldehyde) in an amount providing from about 0.01 to 1.0 parts of formaldehyde per 100 parts of the acrylamide polymer, with 0.05 to 0.5 parts being typical. At higher levels (e.g., 0.05 parts and more) the seal is aseptic, seal adhesion to the ostomy bag (or bag retainer) is improved, the seal composition appears less grainy and more homogeneous, and the seal swells less in water.

The ostomy seal is typically made by blending the particulate acrylamide polymer or polymers and any solid adjuvant (pigment, colorant, antiseptic, stabilizer and the like) being used, and admixing this blend with the polyol, or mixture of polyols, containing water to form a homogeneous admixture. Typically, the polyaldehyde, and the bisulfite if used, are dissolved in the polyol(s)-water mixture before the acrylamide polymer. Other adjuvants, soluble in the glycols and/or water, likewise may be predispersed in the glycol(s)-water mixture. Sometimes, it may be advantageous to prewet and predisperse the polymer and/or solid adjuvants with some or all of the polyol(s) before admixing the water. These and still other techniques of combining and mixing the seal ingredients will be apparent to those skilled in the art.

After all the ingredients are well dispersed, the resulting liquid dispersion is formed into the desired seal configuration, such as ring, pad, gasket and the like, by casting the composition into an appropriate mold and then gelling and crosslinking the composition. If desired, two or more layers of different compositions may be successively cast, or be combined after gelling, to provide a seal having different properties for each face. The time required for gellation will vary depending upon the seal composition—particularly the water level—and temperature. Generally, one or both are set—the rate of gellation increasing as the water level and/or temperature increase—to effect incipient gellation within 5–60 minutes. Typically, gelling and crosslinking are done in one step by treating the cast liquid seal at an elevated temperature, such as 45°–90° C., for a period sufficient to substantially crosslink and water insolubilize the acrylamide polymer. Because low temperatures can require treatment times as long as 48 hours, generally temperatures of about 60° C. or higher are preferred: adequate crosslinking being obtained in one hour @ 60° C. or 30 minutes @ 90° C. Also, these higher crosslinking temperatures are required when formaldehyde is used, if its advantages are to be realized. Preferably, the kind and quantity of polyaldehyde (and quantity of formaldehyde if used), and the time and temperature of crosslinking are chosen to provide an ostomy seal increasing no more than 400 percent in weight after 24 hours immersion in water @ 25° C. and more preferably no more than 300 percent. If necessary, excessive water loss from the seal during crosslinking may be prevented by means such as treating the seal in a high humidity environment or enclosing the seal in a moisture barrier.

Other ingredients may be incorporated into the invention seals, care being taken to choose adjuvants and quantities that are compatible with the seal composition and do not appreciably diminish its desirable physical and chemical properties or significantly inhibit its crosslinking. Thus, the type and quantity of any adjuvant(s) utilized should not increase the seal water swellability, to more than the 400 percent, preferably 300 percent, maximums discussed above. Examples of other ingredients that may be used are: other types of water-soluble polymers both natural and synthetic, such as cornstarch, gelatin, casein, guar gum, carboxy methyl cellulose, high-molecular-weight polyethylene oxide, polyvinyl alcohol, vinyl acetate-maleic halfamide copolymers; antiseptic agents; bactericides; fungicides; polyvalent metal (Ca, Mg, etc.) hydroxides and salts; other types of crosslinking agents, such as methylene bisacrylamide; pigments; dyes; fillers; pH-buffers; tackifiers; deodorants; and the like.

When the seal composition is deficient in tackiness or adhesiveness to the skin and/or the ostomy bag, a suitable adhesive may be applied to one or both faces of the seal by means well-known to the art. For example, the surface of the seal, after being gelled and either before or after being crosslinked, may be coated with a suitable liquid adhesive, which is then dried or polymerized to the solid state. Alternatively, the adhesive layer may be preformed on a release sheet, and the ostomy seal either cast (before gellation), or laminated (after gellation, and either before or after being crosslinked) to the adhesive layer. Illustrative of adhesives that have been used are Swift No. 45508 polyvinyl acetate/polyacrylate adhesive, Dow Corning No. 355 medical-grade adhesive, and 3M's ST-1524 transfer tape.

EXAMPLES 1-9

Nine ostomy rings (about one-quarter inch thick) were made with Reten 420 (virtual acrylamide homopolymer containing not more than four percent sodium acrylate and having a Brookfield viscosity at one percent solids in water at 25° C. of about 300 cps or more) plasticized with a glycerine/propylene glycol mixture containing 5.6 to 8.7 percent water, and crosslinked with glutaraldehyde (examples 1, 2 and 4 to 8) or alpha-hydroxyadipaldehyde (example 3). Example 4, additionally contained paraformaldehyde; example 8, magnesium hydroxide; and examples 6 and 7, sodium metabisulfite in quantities providing mole ratios of 0.5 and 1.0, respectively, of bisulfite to dialdehyde. Example 9, illustrating prior art ostomy seals, contained no dialdehyde.

The dialdehydes and sodium metabisulfite each were first dissolved in part of the water before being admixed with a mixture of the glycerine and propylene glycol containing the balance of the water. Within a few minutes, the Reten 420 (and magnesium hydroxide in example 8) was added, and mixed (about two minutes) until the polymer particles were wetted by and homogeneously dispersed in the plasticizer mixture. The resulting liquid dispersions was cast into ostomy ring molds (2⅜" O.D., 1⅜" I.D. and ¼" deep) and gelled and crosslinked in a hot air oven (except example 9) at the times and temperatures indicated in the Table. After being crosslinked, two-gram sections of the rings were immersed in water at ambient temperature (about 25° C.) and the increase in weight and gel strength measured after varying immersion periods. Further, the color of the rings for Examples 5 to 8, immediately after crosslinking, was observed and recorded.

From the data in the Table, it can be seen from examples 1 to 3 that as little as 0.08 parts of glutaraldehyde crosslinks the acrylamide polymer, but that tighter crosslinking and greater water resistivity are obtained at higher dialdehyde levels; and that alphahydroxyadipaldehyde is equally effective. Example 4 demonstrates the even better water resistance provided by the concurrent use of formaldehyde with dialdehyde. Examples 6 and 7 illustrate the color stabilization provided by sodium metabisulfite and the enhanced stabilization that is obtained when the ratio of bisulfite is increased from one-half to one mole per mole of the crosslinking dialdehyde. Even better results were obtained when the bisulfite was increased to a mole ratio of 1.8:1: ostomy seals showing no discernable yellowing even being aged six hours at 75° C. in a hot air oven. Finally, example 8 illustrates that a filler, such as magnesium hydroxide, may be used in the invention seals with advantage: providing a great increase in the level of plasticizing polyol(s) that may be used, and a diminution of water swelling.

While the invention has been described and illustrated with reference to certain preferred embodiments thereof, e.g., improved acrylamide polymer compositions and sealing means for ostomy appliances, those skilled in the art will appreciate that various changes, modifications and substitutions can be made therein without departing from the invention detailed herein. For instance, the properties possessed by the polymer compositions of the present invention render such compositions and articles shaped therefrom suitable for use in a variety of surgical or medical applications, i.e., pads, wound coverings, bandages, dressings, self-adherent wraps, adhesives for device securement and the like in accordance with the objects and practices of the present invention.

What is claimed is:

1. A shaped polymeric product suitable for application to human skin made from a composition which comprises a water-dispersible acrylamide polymer; a quantity, rendering the composition soft and elastomeric, of a solvating water-miscible polyol, or mixture of polyols, containing water; and a polyaldehyde capable of crosslinking the acrylamide polymer; said polymeric product being treated at a temperature and time sufficient to substantially crosslink and water insolubilize the acrylamide polymer.

2. The shaped polymeric product of claim 1 in which the composition further includes formaldehyde.

3. The shaped polymeric product of claim 1 wherein the polyol comprises at least 50 percent glycerine and one percent water.

4. The shaped polymeric product of claim 3 wherein the acrylamide polymer is a copolymer containing at least 51 percent acrylamide.

5. The shaped polymeric product of claim 3 wherein a mixture of acrylamide polymers is used, and at least 50 percent of the mixture is a virtual homopolymer of acrylamide.

6. The shaped polymeric product of claim 3 wherein the acrylamide polymer is a virtual homopolymer of acrylamide.

7. The shaped polymeric product of claims 1, 2, 3, 4, 5 or 6 in which the composition further includes a stabilizer attenuating product discoloration.

8. In an ostomy drainage device, the improvement comprising employing the shaped polymeric product of claim 7 as a seal for said ostomy drainage device.

9. In an ostomy drainage device, the improvement comprising employing the shaped polymeric product of claims 1, 2, 3, 4, 5, or 6 as the seal for said ostomy drainage device.

10. An adherent pad comprised of the shaped polymeric product of claim 1.

TABLE

| EXAMPLES | 1 | 2 | 3 | 4 | 5 | 6 | 7 | 8 | 9 |
|---|---|---|---|---|---|---|---|---|---|
| Reten 420 | 100 | 100 | 100 | 100 | 100 | 100 | 100 | 100 | 100 |
| glycerine (anhydrous) | 144 | 144 | 144 | 143.7 | 147 | 147 | 147 | 221 | 144 |
| propylene glycol | 16.7 | 16.7 | 16.7 | 16.6 | 16.7 | 16.7 | 16.7 | 25 | 16.6 |
| water | 9.6 | 10.6 | 15.3 | 9.0 | 10.8 | 10.8 | 10.8 | 16.2 | 11.3 |
| glutaraldehyde[1] | 0.08 | 0.41 | —0.44 | 0.41 | 0.41 | 0.41 | 0.62 | — | — |
| alpa-hydroxyadipaldehyde[1] | — | — | 0.82 | — | — | — | — | — | — |
| paraformaldehyde | — | — | — | 0.17 | — | — | — | — | — |
| sodium metabisulfite[1] | — | — | 0.76 | — | 0.40 | 0.80 | — | — | — |
| magnesium hydroxide | — | — | — | — | — | — | — | 50 | — |
| Crosslinking treatment | 40 minutes @ 70° C. | | | 60 minutes @ 70° C. | 30 minutes @ 90° C. | | | | 11 days @ 25° C. |
| Color after crosslinking | — | — | — | — | light yellow | off white | white | yellow | — |
| Weight gain (in percent) after immersion in water (25° C.) for: | | | | | | | | | |
| 8 hours | 245 | 210 | — | 195 | — | — | — | — | 250 |
| 10 hours | — | — | — | — | 250 | 250 | 260 | 200 | — |
| 24 hours | — | — | 225 | 255 | 330 | 350 | 360 | 280 | N.M.[3] |
| 72 hours | 560 | 390 | 400[4] | 300 | 415 | 450 | 465 | 355 | — |
| Gel strength[5] after immersion in water (25° C.) for: | | | | | | | | | |
| 10 hours | | | | | + | + | + | + | —[6] |
| 24 hours | | | | + | + | + | + | + | |
| 72 hours | | | | + | + | + | — | + | |

[1]Glutaraldehyde and alpha-hydroxyadipaldehyde were used as 25% aqueous solutions, while sodium metabisulfite was used as a 35% aqueous solution. The solutions were admixed with the glycerine/propylene glycol/water mixture before the Reten 420.
[2]Ring was not treated at an elevated temperature because of the absence of a dialdehyde crosslinker. After 11 days at 25° C., test rings were completely gelled.
[3]N.M. = Not measurable: sample swelled so much that it could not be handled and weighed.
[4]Weight gain after 132 hours water immersion.
[5]Gel strength measured by centering a 750 gram, 1.9 cm diameter bar upon the center of the water-swollen ring section. A strong ring supports the bar for 30 seconds (denoted by "+"), while a weak ring does not (denoted by "−"). A blank space indicates that the test was not run.
[6]Gel strength after eight hours water immersion.

UNITED STATES PATENT AND TRADEMARK OFFICE
CERTIFICATE OF CORRECTION

PATENT NO. : 4,254,008
DATED : March 3, 1981
INVENTOR(S) : George Krsek

It is certified that error appears in the above-identified patent and that said Letters Patent are hereby corrected as shown below:

Column 2, line 3, "requrements" should be --requirements--.

Column 4, line 21, "poly(s)" should be --polyol(s)--.

Columns 7 and 8, in the Table, following "glutaraldehyde[1]", Table Columns 3-9 should read --

| 3 | 4 | 5 | 6 | 7 | 8 | 9 |
|---|---|---|---|---|---|---|
| ---- | 0.44 | 0.41 | 0.41 | 0.41 | 0.62 | ---- |

--;

following "sodium metabisulfite[1]", Table Columns 3-9 should read --

| 3 | 4 | 5 | 6 | 7 | 8 | 9 |
|---|---|---|---|---|---|---|
| ---- | 0.76 | ---- | 0.40 | 0.80 | ---- | ---- |

--;

following "Crosslinking treatment", Table Column 9, "11 days @ $25°C$" should read --11 days @ $25°C^2$--.

Signed and Sealed this
Second Day of June 1981

[SEAL]

Attest:

RENE D. TEGTMEYER

Attesting Officer

Acting Commissioner of Patents and Trademarks